(12) United States Patent
Shah et al.

(10) Patent No.: US 8,603,185 B2
(45) Date of Patent: Dec. 10, 2013

(54) STENT GEOMETRY

(75) Inventors: Raj J. Shah, Denver, CO (US); Richard W. Ducharme, Winston-Salem, NC (US)

(73) Assignees: Cook Medical Technologies LLC, Bloomington, IN (US); The Regents of the University of Colorado, Denver, CA (US)

( * ) Notice: Subject to any disclaimer, the term of this patent is extended or adjusted under 35 U.S.C. 154(b) by 361 days.

(21) Appl. No.: 12/721,858

(22) Filed: Mar. 11, 2010

(65) Prior Publication Data

US 2011/0224775 A1     Sep. 15, 2011

(51) Int. Cl.
*A61F 2/04*     (2013.01)

(52) U.S. Cl.
USPC ...................................... 623/23.64

(58) Field of Classification Search
USPC ............ 623/1.15, 23.64–23.7; 604/8
See application file for complete search history.

(56) References Cited

U.S. PATENT DOCUMENTS

| | | | |
|---|---|---|---|
| 4,699,611 A | 10/1987 | Bowden | |
| 5,052,998 A | 10/1991 | Zimmon | |
| RE35,849 E | 7/1998 | Soehendra | |
| 5,984,965 A * | 11/1999 | Knapp et al. | 623/23.7 |
| 6,132,471 A | 10/2000 | Johlin, Jr. | |
| 6,945,950 B2 | 9/2005 | Clayman et al. | |
| 7,118,600 B2 * | 10/2006 | Dua et al. | 623/23.68 |
| 7,195,646 B2 * | 3/2007 | Nahleili | 623/23.64 |
| 7,217,250 B2 | 5/2007 | Kolb | |
| 7,722,677 B2 * | 5/2010 | Ward | 623/23.66 |
| 7,967,770 B2 * | 6/2011 | Li et al. | 604/8 |
| 8,057,461 B2 * | 11/2011 | Deal | 604/544 |
| 2004/0193283 A1 * | 9/2004 | Rioux et al. | 623/23.66 |
| 2005/0113933 A1 | 5/2005 | Carter et al. | |
| 2006/0167538 A1 | 7/2006 | Rucker | |
| 2007/0016306 A1 * | 1/2007 | Dua et al. | 623/23.68 |
| 2008/0086214 A1 * | 4/2008 | Hardin et al. | 623/23.7 |
| 2008/0091275 A1 * | 4/2008 | Ducharme | 623/23.7 |
| 2010/0114325 A1 * | 5/2010 | Yang et al. | 623/23.7 |
| 2010/0145467 A1 * | 6/2010 | Davoudi et al. | 623/23.7 |
| 2010/0211097 A1 * | 8/2010 | Hadba et al. | 606/232 |
| 2010/0211098 A1 * | 8/2010 | Hadba et al. | 606/232 |
| 2011/0125135 A1 * | 5/2011 | Ahmed et al. | 604/544 |

FOREIGN PATENT DOCUMENTS

WO    WO 91/15254 A1    10/1991
WO    WO 2009/029744 A1    3/2009

OTHER PUBLICATIONS

International Search Report mailed Jul. 11, 2011 for International Application No. PCT/US2011/027129.
Written Opinion mailed Jul. 11, 2011 for International Application No. PCT/US2011/027129.

* cited by examiner

*Primary Examiner* — Suzette J Gherbi
(74) *Attorney, Agent, or Firm* — Brinks Gilson & Lione

(57) ABSTRACT

A non-expandable stent and a method for implanting the stent are provided. The stent includes a generally tubular body having a lumen defined therethrough. The body includes a proximal portion having a curved portion configured for placement proximal to a sphincter. The body further includes a distal portion having retaining member extending outward from a proximal end of the distal portion. The retaining member is configured for placement distal to the sphincter and for engagement of the sphincter.

17 Claims, 4 Drawing Sheets

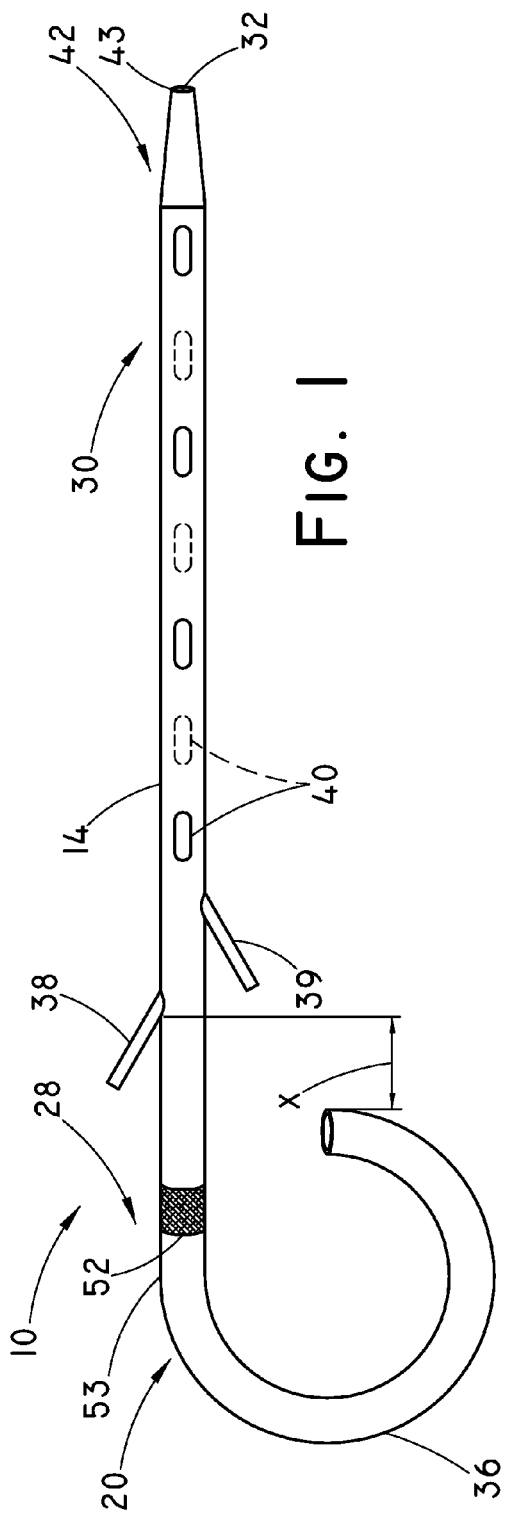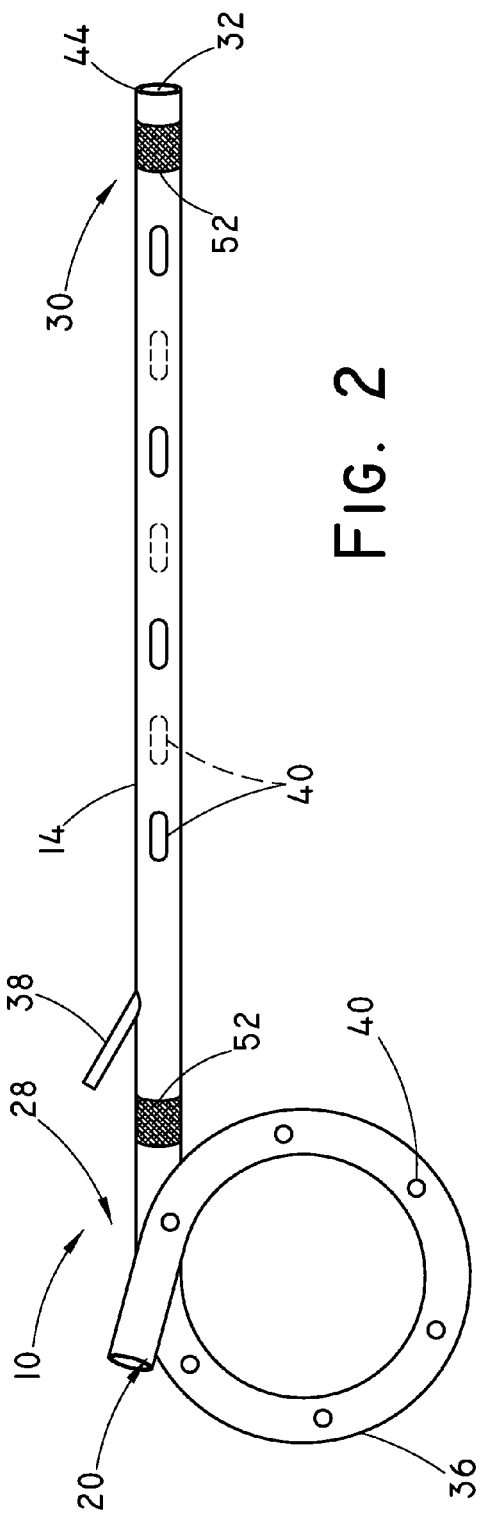

STENT GEOMETRY

TECHNICAL FIELD

This invention generally relates to stents that are implantable in a vessel or duct within the body of a patient, and in particular to stents that may be used to maintain patency of the vessel or duct.

BACKGROUND

Prosthetic devices may be placed in vessels and ducts for a number of medical procedures. Typically, placement of the prosthetic devices into the vessels and ducts functions to maintain an open passage through the vessel or duct. For example, where a biliary or pancreatic duct becomes occluded, it is often desirable to facilitate drainage through the duct by the placement of a tubular prosthesis within the occluded area. In some procedures, stents have been used to maintain an open passage.

The passageways into which the stents are placed may change shape and move in response to bodily movement of the patient. Stents designed for placement in these passageways are flexible to accommodate movement of the passageway. Stents are commonly made of polymers or metals, typically a shape memory alloy, and may include flaps or barbs at each end of the stent which serve to prevent migration and retain the stent in place. Some stents may have various preformed retaining configurations, such as pigtails or spirals, to help maintain the stent in position. Stents have also been formed into various expandable configurations so that, when the stent has reached the occluded area, the stent is expanded to press outwardly against the ductal wall and to thereby maintain its position within the duct. Biliary and pancreatic stents may be delivered using a catheter that may include a pusher from behind the stent that pushes against the proximal end of the stent until the stent has reached its desired location.

During the placement procedure, retaining elements, such as flaps and pigtails have been known to have an abrasive effect on the surrounding ductal tissue as they pass into the duct and through the obstruction or stricture, thus causing or aggravating inflammation of the duct. These retaining elements have also been known to cause aggravation inside the duct to tissue adjacent the retaining elements while the stent is left in place, and particularly, when the stent is removed.

There is a need for an improved stent which can be atraumatically placed within an occluded biliary or pancreatic duct and remain in place without causing aggravation to the ductal tissue, and which further can be removed with little damage or additional irritation to the duct. There is also a need for a stent having retaining elements for engaging a sphincter to hold the stent in position within the duct without causing aggravation to the ductal tissue.

SUMMARY OF THE INVENTION

Accordingly, it is an object of the present invention to provide a stent and method having features that resolve or improve on one or more of the above-described drawbacks.

The foregoing object is obtained in one aspect of the present invention by providing a non-expandable stent that includes a generally tubular body having a lumen defined therethrough. The body includes a proximal portion having a curved portion configured for placement proximal to a sphincter. The body further includes a distal portion having retaining member extending outward from a proximal end of the distal portion. The retaining member is configured for placement distal to the sphincter and configured for engaging the sphincter.

In another aspect, a method of implanting a stent through a sphincter is provided. The method includes providing a stent delivery system having a wireguide and a non-expandable stent slidably positionable over the wire guide. The stent includes a generally tubular body having a lumen defined therethrough. The body includes a proximal portion having a curved portion configured for placement proximal to a sphincter. The body further includes a distal portion having a first retaining member extending outward from a proximal end of the distal portion. The first retaining member is configured for placement distal to the sphincter and configured to engage the sphincter. A remainder of the distal portion, distal to the first retaining member is free of retaining members. The method further includes advancing the delivery system to a sphincter delivery site using an introducer catheter, deploying the stent into the sphincter delivery site by distally advancing the first retaining member through the sphincter and engaging the sphincter and withdrawing the wireguide and the introducer catheter so that the curved portion resumes a curved configuration and is positioned proximal to the sphincter.

In another aspect, a non-expandable stent is provided. The stent includes a generally tubular body having a lumen defined there through. The body includes a proximal portion having a curved portion configured for placement proximal to a sphincter, the curved portion sized and shaped to prevent ingress of the curved portion through the sphincter. The body further includes a distal portion having a retaining member extending outward from a proximal end of the distal portion, the retaining member longitudinally spaced from the curved portion by a distance between about 0-15 mm where a remainder of the distal portion is free of retaining members.

BRIEF DESCRIPTION OF THE DRAWINGS

FIG. 1 is a side view of a stent according to the present invention:

FIG. 2 is a side view of an alternative embodiment of the sent of the present invention;

DETAILED DESCRIPTION OF THE EMBODIMENTS

Figure 3:
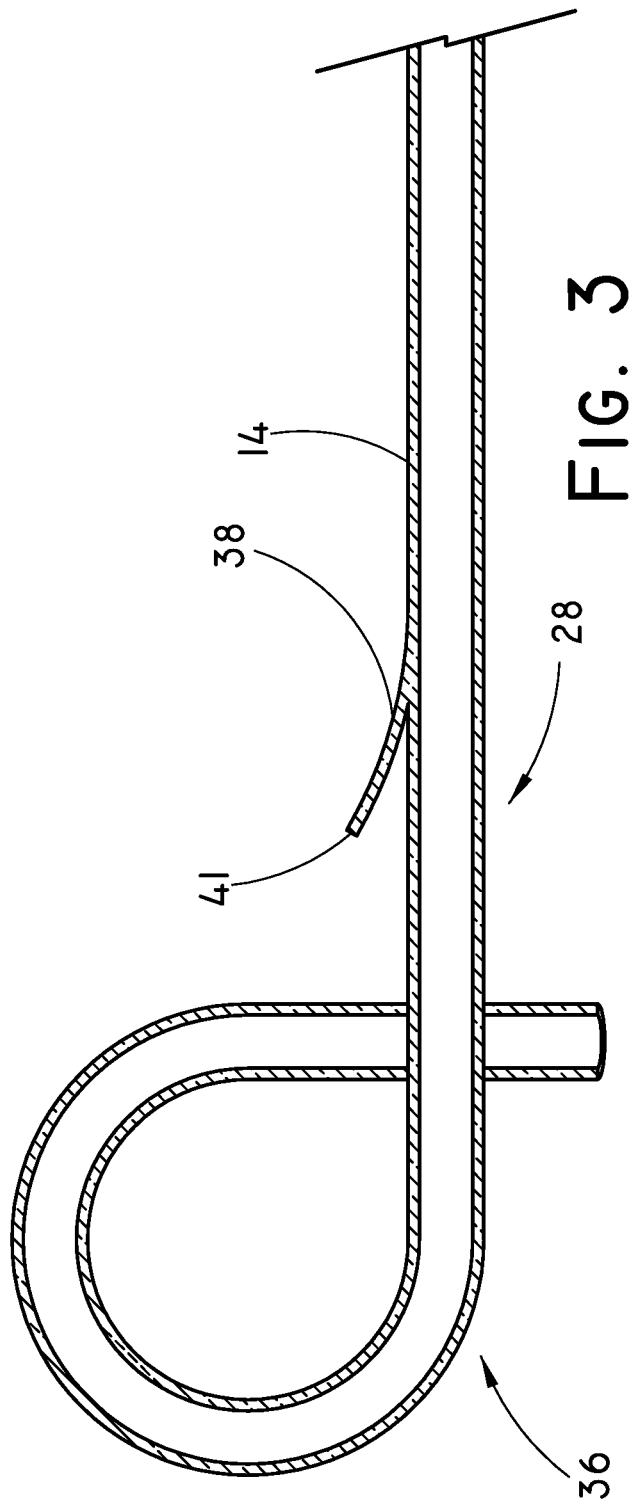
FIG. 3 is a partial view of the stent showing the blunt end of the retaining member.

The invention is described with reference to the drawings in which like elements are referred to by like numerals. The relationship and functioning of the various elements of this invention are better understood by the following detailed description. However, the embodiments of this invention are not limited to the embodiments illustrated in the drawings. It should be understood that the drawings are not to scale, and in certain instances details have been omitted which are not necessary for an understanding of the present invention, such as conventional fabrication and assembly.

As used in the specification, the terms proximal and distal should be understood as being in the terms of a physician delivering the stent to a patient using a deployment system. Hence the term distal means the portion of the stent that is farthest from the physician and the term proximal means the portion of the stent that is nearest to the physician.

FIGS. 1 and 2 illustrate a non-expandable stent 10 in accordance with embodiments of the present invention. The stent 10 includes a generally tubular body 14 having a proximal portion 20 and a distal portion 30. A lumen 32 extends through at least a portion of the tubular body of the stent 10. The proximal portion 20 includes a curved portion 36 and is configured for placement proximal to a sphincter as described in more detail below. A first retaining member 38 is positioned at a proximal end 28 of the distal portion 30 of the tubular body 14. A second retaining member 39 may also provided at the proximal end 28 of the distal portion 30 in some embodiments as shown in FIG. 1. The distal portion 30 is substantially straight and the remainder of the distal portion 30, distal to the retaining member 38, or distal to the second retaining member 39 when present, is free of retaining members. The substantially straight portion may conform to the contours of the duct when the stent 10 is implanted. The term "substantially straight" refers to a portion that is free of loops, such as a pigtail loop that may be formed at the curved portion 36. One or more openings 40 may be included in the stent 10.

As shown in FIG. 1, the curved portion 36 may be about a 270° loop at the proximal portion 20. In some embodiments, the curved portion 36 may be formed as a complete circular loop of about 360° or greater as shown in FIG. 2. The curved portion 36 may also be less than 270°, for example between about 90-270°. The curved portion 36 is configured for placement proximal to a sphincter and sized and shaped to help prevent inward migration of the stent 10 from the placement position within the patient (see FIG. 6). Additional degrees of loop formation for the curved portion 36 are also possible where the curved portion 36 helps maintain the position of the stent 10. One purpose of the curved portion 36 of the stent 10 is to remain in the duodenum or other relatively larger passageways proximal to the sphincter to prevent the stent 10 from entirely entering the relatively smaller duct. Preventing the stent 10 from entering the smaller duct avoids a potential for surgical intervention to remove the stent 10 from the smaller duct.

The curved portion 36 may be configured to work together with the retaining member 38 that is provided at the proximal end 28 of the distal portion 30 to help prevent migration of the stent 10 once the stent 10 has been positioned in the duct. The retaining member 38 extends generally radially outward from the tubular body 14 of the stent 10 and is configured for placement distal to the sphincter and for engaging the sphincter. The retaining member 38 may extend radially outward at an angle of about 5-90° relative to the tubular body 14. One, two or more retaining members 38, 39 may be provided at the proximal end 28 of the distal portion 30.

Figure 4:
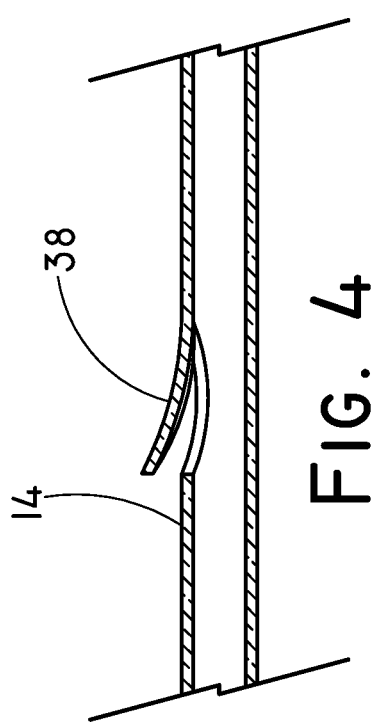
FIG. 4 is a cross-sectional view of the retaining member of the stent.

In some embodiments, one retaining member 38 may extend outward from the tubular body 14. The retaining member 38 may be a flap that extends a length of about 4-8 mm from the tubular body 14. Other lengths for the retaining member may be possible and may depend on the size of the duct opening, the flexibility of the retaining member, the length of the stent and the amount of time the stent 10 is to remain implanted within the duct. The retaining member 38 may be formed from the tubular member 14 with a longitudinal cut in the wall of the tubular member 14 as shown in FIG. 3. Alternatively, the retaining member may be formed by molding with the body 14 or addition to the tubular body 14 or any method known to one skilled in the art. The retaining member 38 may have a curvilinear cross-sectional profile similar to the tubular body 14 as shown in FIG. 4. The curvilinear profile may also help to retain the retaining member 38 in position against the sphincter. In some embodiments, the retaining member 38 may include a squared-off, blunt end 41 to contact the sphincter. The blunt end 41 may help reduce retaining member folding away from the sphincter and to increase anchorability of the retaining member 38. The retaining member 38 may be configured for retention of the distal portion 30 within the duct for several days and then allow the stent 10 to pass naturally out of the duct.

When two or more retaining members 38, 39 are provided, the retaining members 38, 39 may be provided circumferentially around the proximal portion 28 of the distal portion 30. For example, a first retaining member 38 may extend radially outward at a direction about 180° opposite the direction of the curved portion 36 as shown in FIG. 1. The second retaining member 39 may extend radially outwardly at about 180° from the first retaining member 38 and in the same direction as the curved portion 36. In some embodiments, a distance x between the curved portion 36 and the retaining member 38 is about 0-15 mm, and in some embodiments, about 5-10 mm. One purpose of the retaining member 38 is to engage the sphincter to hold the stent 10 in the duct so that the stent 10 does not migrate out of the duct in response to bodily movement. The retaining member 38 may contact the sphincter at the opening of the duct and the curved portion 36 may be positioned proximal to the sphincter to hold the stent 10 in position without irritating the interior of the duct and to facilitate later removal of the stent 10. The distal portion 30 of the stent 10 distal to the retaining member 38, or the second retaining member 39 when present, is provided free of retaining members and curved portions to further avoid irritation of the ductal tissue. The retaining member 38 may be sufficiently flexible to collapse against the proximal end 28 for delivery of the stent 10 and yet have sufficient resiliency to contact the sphincter and to hold the stent 10 in place once positioned at the delivery site.

In some embodiments, the distal portion 30 may include a tapered end 42 as shown in FIG. 1. The tapered end 42 may be reduced in some embodiments in size from the distal portion 30 to a distal end 43. By way of non-limiting example, a distal portion 30 of about 10 Fr may be reduced to a distal end 43 that is about 5 Fr. As shown in FIG. 2, the distal portion 30 may also include a straight end 44. As shown in FIGS. 1 and 2, the distal portion 30 is relatively smooth so that the stent 10 does not irritate the duct or vessel walls against the distal portion 30. The distal portion 30 may be positioned against an end of a duct, such as the pancreatic duct, and the proximal end portion 20 may extend into the duodenum as will be discussed below.

The stent 10 may also be provided with a plurality of openings 40 to facilitate drainage from the duct into the duodenum. The openings 40 may be alternating on opposite sides of the stent 10. Alternatively, the openings 40 may be provided in a spiral configuration along the stent 10. In some embodiments, the openings 40 may be provided on the distal end 30. In some embodiments, the one or more openings may be provided in the distal portion 30 and/or the proximal portion 20. The number of openings 40 will depend on the size of the stent 10. The stent 10 will be provided with enough rigidity to maintain the passageway though the duct and keep the lumen 32 open, yet may include openings 40 to facilitate drainage, as will be understood by one skilled in the art. For example, the openings 40 may be spaced apart having about 2 cm between the openings 40. The openings 40 may be provided about 1 cm proximal from the distal end 43. These measurements are provided by way of example and other measurements are possible within the scope of the present invention. In some embodiments, the stent 10 may be free of openings so that the fluid enters the lumen 32 at the distal portion 30 and drains out through the lumen 32 opening at the proximal portion 20.

The stent 10 may also include one or more radiopaque markings 52 to enable the stent 10 to be visualized using fluoroscopy or x-ray. In some embodiments, the radiopaque marker may be provided at the tubular body 14, for example, between the curved portion 36 and the retaining member 38 to help with placement of the stent 10 in the duct. In some embodiments, the stent 10 may include the radiopaque marking 52 at the distal portion 30 to provide an indication of how far the stent 10 has traveled within the patient's duct. In some embodiments, the stent 10 itself may be radiopaque. Some embodiments may include visual markings created by a laser or ink that may be visualized so the stent 10 may be visualized using fluoroscopy or x-ray. One marking 52 may be included at a base 53 of the curved portion 36 to facilitate placement of the curved portion 36 as described below. The stent 10 is delivered with the curved portion 36 straightened for delivery and the marking 52 at the base 53 facilitates positioning of the stent 10 so that the curved portion 36 reforms in the proper position when the delivery system is removed. Any type of visualization marking known to one skilled in the art may be used with the stent 10.

The stent 10 may be of any size suitable for implantation into a duct or passageway such as the biliary or pancreatic ducts. The stent 10 may have an outer diameter of about 3-5 Fr, although larger stents may be used, for example, about 5-7 Fr, about 7-10 Fr and the like. The length of the stent 10 may be about 3-18 cm depending on the diameter. Shorter or longer stents may also be used. The retaining member 38 for a biliary duct may be about 6-8 mm and for a pancreatic duct about 4-6 mm.

The stent may be made from materials so that the stent is soft enough to conform to the curvature of the duct and eliminate or reduce irritation at the implantation site that occurs with a rigid stent, thus reducing the risk of pancreatitis, morphological or ductal changes. The materials should also have sufficient strength to maintain a lumen through the stent when the stent is positioned within the duct. Suitable materials for the stent of the present invention include, but are not limited to the following, SOF-FLEX™, a type of polyether urethane, silicone, block co-polymers, urethanes, polyethylene, polystyrene, polytetrafluoroethylene (PTFE), FEP and the like and combinations thereof.

The stent 10 may be delivered to the implantation site using any delivery system known in the art. The delivery system used will depend on the size of the stent 10 and the materials used to form the stent 10. The delivery system 100 includes a wire guide 110 and an introducer catheter 120. The wire guide 110 extends through a lumen 122 in the introducer catheter 120 and the lumen 32 in the stent 10 for directing the delivery of the stent 10 through the passageways to the body site for placement of the stent 10. During delivery to the site, the stent 10 is placed over the wireguide 110 and the curved portion 36 of the stent 10 is temporarily straightened. Once the wire guide 110 and the introducer catheter 120 have been removed from the stent 10 at the delivery site, the curved portion 36 resumes the curved configuration. The wireguide 110 and the introducer catheter 120 have lengths sufficient to extend from the desired location in the patient's body to the exterior of the patient, as will be understood by one skilled in the art. The delivery system 100 may also include additional lumens.

Figure 5:
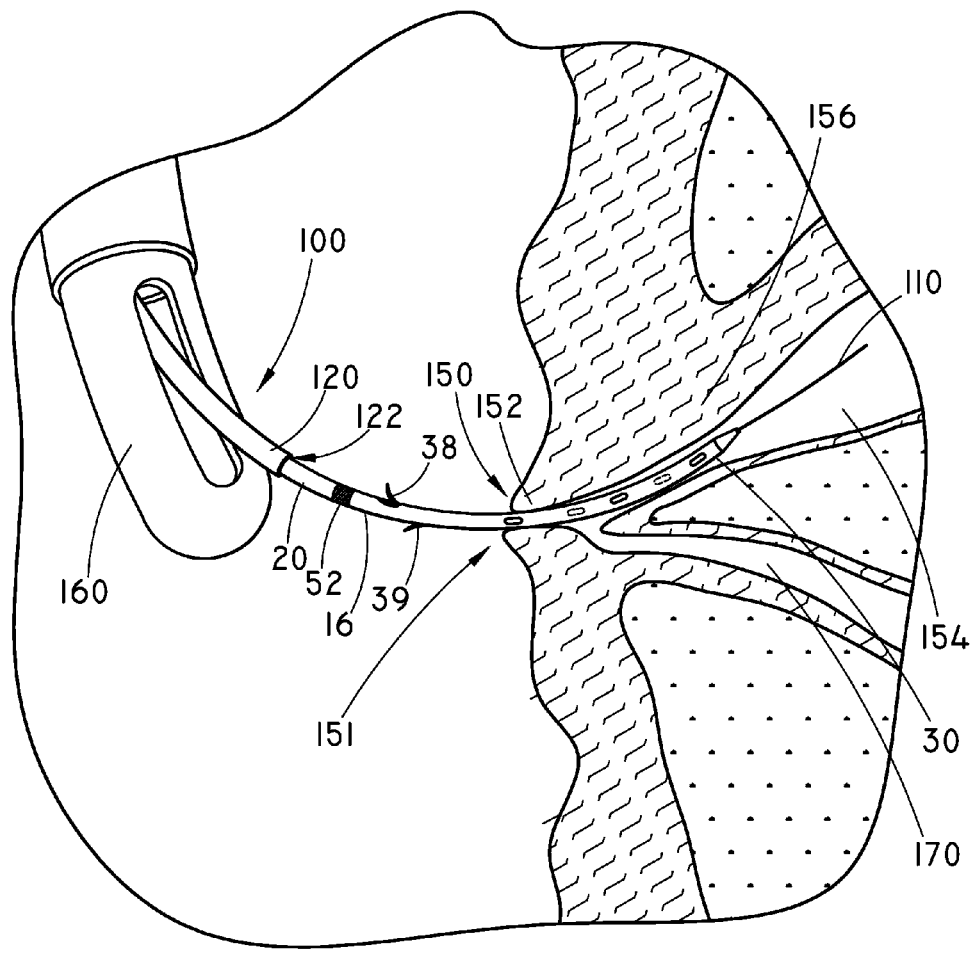
FIG. 5 is a diagrammatic view of a wireguide advanced through the occluded area of a biliary duct.
Figure 6:
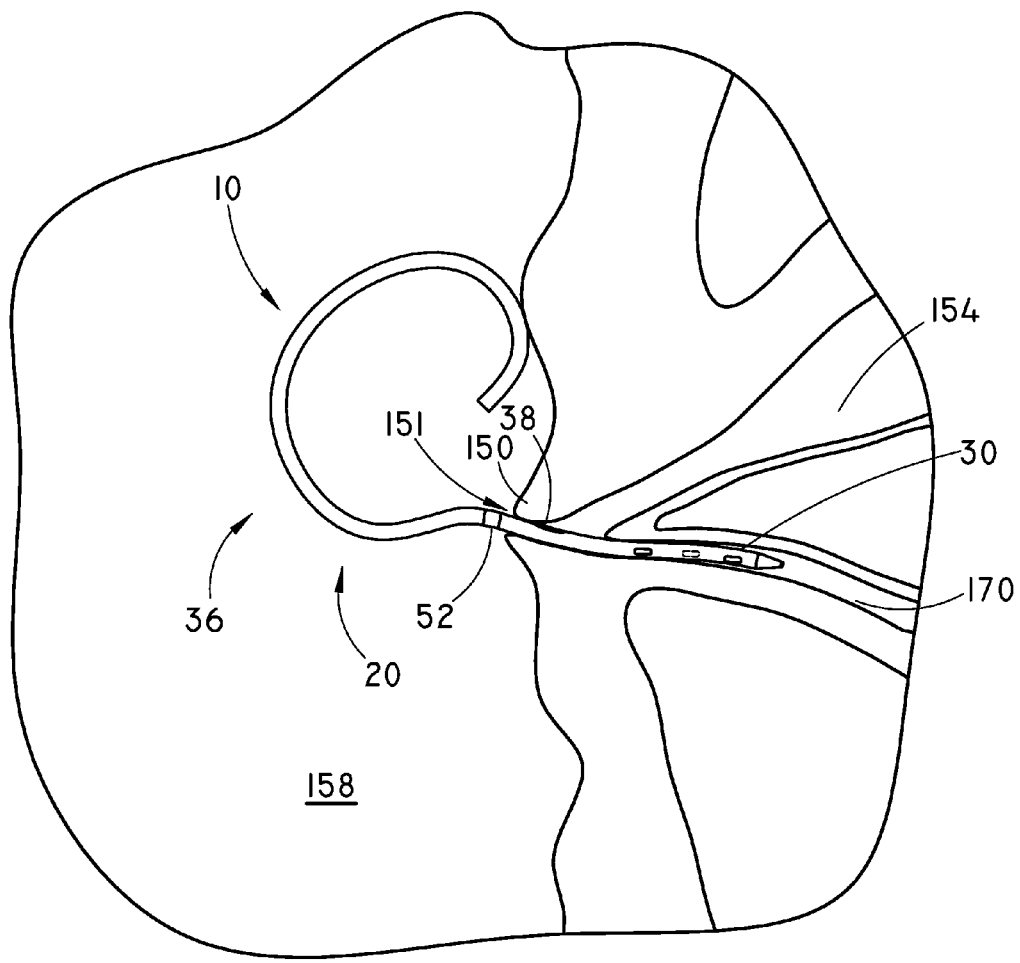
FIG. 6 is a diagrammatic view of the stent placed within the biliary duct.

An exemplary method of delivering and implanting the stent 10 of the present invention will be illustrated with reference to the delivery system 100. As shown in FIGS. 5 and 6, the delivery system 100 may be used to place the stent 10 in the biliary duct 150 at the Sphincter of Odi 151. As shown in FIG. 5, the wireguide 110 has been advanced through the Sphincter of Odi 151 past a papilla 152 and into the common bile duct 154. The stent 10 is advanced over the wireguide 110 and out of an endoscope 160 by the introducer catheter 120. The introducer catheter 120 advances the stent 10 into position by pushing the stent 10 distally along the wireguide 110 until the implantation site is reached. The stent 10 may be advanced until the retaining member 38 is through the sphincter 151 and expands outward to contact the sphincter 151 (see, for example, FIG. 6 with the retaining member in position against the sphincter). The distal portion 30 of the stent 10 is advanced though a stricture 156 in the duct 154. The radiopaque marker 52 may be used to help determine the position of the stent 10 within the duct 154.

Once the stent 10 has been positioned within the duct 154, the introducer catheter 120 and the wireguide 110 are retracted through the endoscope 160, leaving the stent 10 in position within the duct with the retaining member 38 positioned distal to and engaging the sphincter 151. As shown in FIG. 6, the stent 10 may also be placed in a pancreatic duct 170. As shown, the curved portion 36 resumes the curved configuration once the wireguide 110 has been withdrawn and the curved portion 36 is positioned proximal to the sphincter 151. The curved portion 36 remains in the duodenum 158 and a portion of the curved portion 36 may abut the sphincter 151 while the retaining member 38 engages the distal portion of the sphincter 151 to hold the stent 10 in position. The distal portion 30 of the stent 10 extends past the stricture 156 to maintain a passageway therethrough. As shown, the retaining member 38 contacts the sphincter 151 thereby reducing irritation within the duct 170 that may occur if retaining members are provided on the stent body 34 or at the distal end portion 30. The stent 10 of the present invention shown positioned within the duct 170 is free of retaining members on the distal portion 30 distal to the retaining member 38. Irritation of the duct is also reduced since a retaining member is not pushed along the duct causing further irritation of the duct, such as when a retaining member is included on the distal end of the stent. The curved portion 36 and the retaining member 38 of the stent 10 provide the stent 10 with sufficient structure to hold the stent 10 within the duct in the proper position. Similarly, the curved portion 36 and the retaining member 38 allow for easy removal of the stent 10 with a minimal irritation to the ductal tissue. The retaining member 38 need only to pass through the sphincter 151 for removal, leaving the remaining ductal tissue untouched by any protruding retaining members.

The above Figures and disclosure are intended to be illustrative and not exhaustive. This description will suggest many variations and alternatives to one of ordinary skill in the art. All such variations and alternatives are intended to be encompassed within the scope of the attached claims. Those familiar with the art may recognize other equivalents to the specific embodiments described herein which equivalents are also intended to be encompassed by the attached claims. For example, the invention has been described in the context of the biliary system for illustrative purposes only. Application of the principles of the invention to any other bifurcated lumens or vessels within the body of a patient, including areas within the digestive tract such as the pancreatic system, as well as areas outside the digestive tract such as other vascular systems, by way of non-limiting examples, are within the ordinary skill in the art and are intended to be encompassed within the scope of the attached claims.

The invention claimed is:

1. A non-expandable stent comprising:
a generally tubular body having a lumen defined therethrough, the body comprising:
a proximal portion comprising a curved portion, the curved portion comprising a loop configured for placement proximal to a sphincter to prevent ingress of the curved portion through the sphincter; and
a substantially straight distal portion comprising a first retaining member extending outward from a proximal end of the distal portion, the first retaining member configured for placement distal to the sphincter and configured to engage the sphincter such that the curved portion and the first retaining member engage the sphincter to hold the stent in position,
wherein the distal portion, distal to the first retaining member is free of retaining members and the distal portion distal to the first retaining member has a first length that is greater than a second length, the second length extending longitudinally between the curved portion and the first retaining member.

2. The stent of claim 1, further comprising a second retaining member extending outward from the proximal end of the distal portion, the second retaining member positioned proximal to the first retaining member.

3. The stent of claim 1, further comprising a second retaining member extending outward from the proximal end of the distal portion, the second retaining member positioned about 180° circumferentially apart from the first retaining member.

4. The stent of claim 1, further comprising a tapered distal end.

5. The stent of claim 1, further comprising a plurality of openings in the tubular body.

6. The stent of claim 5, wherein the plurality of openings are alternately spaced apart on opposite sides of the tubular body.

7. The stent of claim 1, wherein the curved portion comprises about a 90° to 270° loop.

8. The stent of claim 1, wherein the curved portion comprises about a 270° loop or greater.

9. The stent of claim 1, wherein an outer diameter of the stent is between about 3 French to about 10 French.

10. The stent of claim 1, wherein an outer diameter of the stent is about 5 French or less.

11. The stent of claim 1, wherein the second length is between about 0-15 mm.

12. The stent of claim 11, wherein the second length is between about 5-10 mm.

13. The stent of claim 1, wherein the stent comprises a material selected from the group consisting of plastics, silicone, block polymers, urethanes, polystyrene, polyethylene, PTFE, FEP and combinations thereof.

14. A method for implanting a stent through a sphincter, the method comprising;
providing a stent delivery system having a wireguide; and
a non-expandable stent slidably positionable over the wireguide, the stent comprising:
a generally tubular body having a lumen defined therethrough, the body comprising:
a proximal portion comprising a curved portion, the curved portion configured for placement proximal to a sphincter to prevent ingress of the curved portion through the sphincter; and
a substantially straight distal portion comprising a first retaining member extending outward from a proximal end of the distal portion, the first retaining member configured for placement distal to the sphincter and configured to engage the sphincter, and a remainder of the distal portion, distal to the first retaining member free of retaining members
advancing the delivery system to a sphincter delivery site using an introducer catheter;
deploying the stent into the sphincter delivery site by distally advancing the first retaining member through the sphincter and engaging the sphincter with the curved portion positioned proximal to the sphincter and the first retaining member, the first retaining member positioned distal to the sphincter, the first retaining member being a distalmost retaining member and distally extending the distal portion free of retaining members into a duct; and
withdrawing the wireguide and introducer catheter so that the curved portion resumes a curved configuration and is positioned proximal to the sphincter.

15. The method of claim 14, further comprising visualizing a radiopaque portion provided on the delivery apparatus for positioning the stent at the delivery site.

16. The method of claim 14, comprising positioning the stent in a biliary or pancreatic duct.

17. The method of claim 14, comprising positioning the stent wherein the curved portion is positioned in the duodenum.

* * * * *

UNITED STATES PATENT AND TRADEMARK OFFICE
CERTIFICATE OF CORRECTION

PATENT NO. : 8,603,185 B2
APPLICATION NO. : 12/721858
DATED : December 10, 2013
INVENTOR(S) : Raj J. Shah et al.

Page 1 of 1

It is certified that error appears in the above-identified patent and that said Letters Patent is hereby corrected as shown below:

On the Title Page

Left Column, item (73), replace "Denver, CA" with --Denver, CO--.

Signed and Sealed this
Twenty-fourth Day of April, 2018

Andrei Iancu
*Director of the United States Patent and Trademark Office*